United States Patent
Wei et al.

(10) Patent No.: US 10,441,946 B2
(45) Date of Patent: Oct. 15, 2019

(54) LINEAR ALPHA-OLEFIN CATALYSTS AND PREPARATION AND USE THEREOF

(71) Applicant: APALENE TECHNOLOGY CO., LTD. (JIAXING), Jiaxing (CN)

(72) Inventors: Dongchu Wei, Jiaxing (CN); Bing Li, Jiaxing (CN)

(73) Assignee: APALENE TECHNOLOGY CO., LTD. (HANGZHOU), Hangzhou (CN)

( * ) Notice: Subject to any disclaimer, the term of this patent is extended or adjusted under 35 U.S.C. 154(b) by 0 days.

(21) Appl. No.: 15/731,880

(22) PCT Filed: Apr. 1, 2016

(86) PCT No.: PCT/CN2016/000184
§ 371 (c)(1),
(2) Date: Aug. 18, 2017

(87) PCT Pub. No.: WO2017/161466
PCT Pub. Date: Sep. 28, 2017

(65) Prior Publication Data
US 2018/0147571 A1    May 31, 2018

(30) Foreign Application Priority Data

Mar. 22, 2016 (CN) .......................... 2016 1 0164561
Mar. 22, 2016 (CN) .......................... 2016 1 0165648
Mar. 22, 2016 (CN) .......................... 2016 1 0165991

(51) Int. Cl.
*B01J 31/18* (2006.01)
*B01J 31/22* (2006.01)
*B01J 31/26* (2006.01)
*C07C 2/32* (2006.01)
*B01J 31/14* (2006.01)

(52) U.S. Cl.
CPC ........... *B01J 31/184* (2013.01); *B01J 31/143* (2013.01); *B01J 31/183* (2013.01); *B01J 31/1815* (2013.01); *B01J 31/22* (2013.01); *B01J 31/26* (2013.01); *C07C 2/32* (2013.01); *B01J 2231/20* (2013.01); *B01J 2531/842* (2013.01); *C07C 2523/745* (2013.01); *C07C 2531/14* (2013.01); *C07C 2531/22* (2013.01); *Y02P 20/52* (2015.11)

(58) Field of Classification Search
CPC ...... B01J 31/184; B01J 31/183; B01J 31/143; B01J 31/1815; B01J 31/22; B01J 31/26; B01J 2231/20; B01J 2531/842; C07C 2/32; C07C 2523/745; C07C 2531/14; C07C 2531/22; Y02P 20/52
IPC ....................... C07C 2/32,11/02, 11/107, 11/08
See application file for complete search history.

(56) References Cited

U.S. PATENT DOCUMENTS

| | | | | |
|---|---|---|---|---|
| 2006/0229480 A1* | 10/2006 | Blann | ...................... | B01J 31/14 585/535 |
| 2013/0172651 A1* | 7/2013 | Small | ...................... | C07C 2/32 585/523 |
| 2013/0303817 A1* | 11/2013 | Shaik | ...................... | C07C 2/08 585/504 |
| 2014/0316087 A1* | 10/2014 | Li | ...................... | C08F 110/02 526/155 |

* cited by examiner

*Primary Examiner* — In Suk C Bullock
*Assistant Examiner* — Ali Z Fadhel
(74) *Attorney, Agent, or Firm* — Panterrain IP Law; Charles Liu

(57) ABSTRACT

The present invention relates to a novel linear α-olefin catalyst composition, and preparation and use thereof. The catalyst composition includes a main catalyst and a co-catalyst, wherein the main catalyst is an imino-based iron coordination compound, and the co-catalyst is a mixture of methylaluminoxane, triisobutylaluminum, and borane or $GaCl_3$. The catalyst composition can be used to catalyze ethylene oligomerization to produce linear α-olefins having a selectivity of greater than 96%, carbon distribution between C4-C28 with the component of C6-C20 being greater than 75%. The catalyst of the invention is stable in structure and can be used for ethylene oligomerization with high catalytic efficiency. The method of the invention has the advantages of relatively convenient in operation, readily available of raw materials, high yield, low costs, less pollution and easy for industrial production.

10 Claims, No Drawings

LINEAR ALPHA-OLEFIN CATALYSTS AND PREPARATION AND USE THEREOF

FIELD OF THE INVENTION

The present invention relates to the field of industrial catalysts, and more particularly to novel linear alpha olefin catalysts, preparation and use thereof.

BACKGROUND OF THE INVENTION

Linear α-olefin (LAO) refers to C4-C28 and above high-carbon straight chain olefins, as important organic chemical raw materials rapidly grown in nearly 30 years. The uses of alpha-olefins are primarily in the following five categories: 1) Used as co-monomers for making linear low density polyethylene (LLDPE) and high density polyethylene (HDPE), mainly including 1-butene, 1-hexene and 1-octene; 2) used for the production of detergents and detergent alcohols with excellent biodegradability; 3) used for making lubricants, as poly-α-olefins are high-quality synthetic lubricants, mainly including 1-decene and 1-octene oligomers; 4) used for making plasticizer alcohols, which have low volatility and good light stability and oxidation resistance when obtained from C8-C10 linear α-olefins; 5) used for making lubricant additives, drilling fluids, adhesives, sealants and the like. More than 50% of the α-olefins used as a copolymer of polyethylene.

The methods of manufacturing α-olefins include wax cracking, alkane dehydrogenation, ethylene oligomerization and extraction. Currently ethylene oligomerization is the major method for producing α-olefin, which accounts for 94.1% of the total α-olefins produced. The catalysts used in the processes are mainly those of alkyl aluminum, titanium, iron, nickel, chromium, etc. With different catalysts and steps, the technologies of ethylene oligomerization include Ziegler process of CPChem, improved Ziegler process of INEOS, and SHOP process of Shell, Idemitsu process of Idemitsu Petrochemical, and Versipol process of Dupond. The Shell's SHOP process, being complex and long in procedure, contains additional steps such as disproportionation and isomerization in addition to the oligomerization process, and thus is highest in the costs of production, but, on the other hand, has advantages in quality and distribution of products, and is able to convert α-olefins for isomerised olefins. Researches on the catalysts of ethylene oligomerization for making α-olefins showed much progress in recent years, there had been reports and patents on non-homogeneous methods of olefin oligomerization for making α-olefins. With rapid advance of the polyethylene (PE) industry, α-olefins, especially 1-hexene and 1-octene, are now highly in demand. Co-polyethylene of 1-hexene is presently the fastest growing product. There are totally 13 sets of α-olefin production facilities of 11 manufacturers in the world, primarily in North America, Europe, South Africa and Japan. In 2009, the annual α-olefin production capacity in the world is 4,334 kt/a, which became over 4,914 kt/a in 2010.

With the rapid growth of the polyolefin and surfactant industries, there are increasing demands on $C_6$-$C_8$α-olefins as polyolefin comonomers and $C_{10}$-$C_{18}$α-olefins as major materials for detergents. Thus, it has significant economic and technological value to enhance the content of such linear α-olefins in the products.

SUMMARY OF THE INVENTION

The present invention is to provide a catalyst composition, and preparation and applications thereof, for improving relative content of the $C_6$-$C_{18}$ linear α-olefins in the products. Such catalyst composition can be used in ethylene oligomerization for linear α-olefins production to meet the needs in the industry.

The present invention relates to a series of iron-based catalyst compositions and application for ethylene oligomerization, wherein the main catalyst is iron (II) imino coordination compound, and the co-catalyst is methylaluminoxane, tri-isobutyl chloride and borane or $GaCl_3$ mixture. Such catalyst compositions are used for catalysis of ethylene oligomerization to cause the carbon number distribution of the linear α-olefins being $C_4$-$C_{28}$, wherein, the fraction of $C_6$-$C_{20}$ is over 80% in weight.

The present invention provided novel linear poly-α-olefin catalysts, comprising a main catalyst and a co-catalyst, wherein the main catalyst is an imino-based iron coordination compound having a general formula (I):

(I)

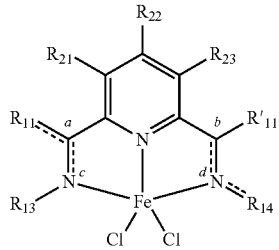

(I)

wherein, the substituents are further defined in (A), (B) or (C) as follows:

(A):

$R_{21}$ and $R_{22}$, and $R_{22}$ and $R_{23}$ are respectively connected to aromatic rings, which together form a fused ring structure;

$R_{11}$ is hydrogen, $C_1$-$C_5$ alkyl, isopropyl or trifluoromethyl, $R_{13}$ is phenyl, wherein $R_{11}$ and the a-position carbon are linked with a single bond, and the a-position carbon and the c-position nitrogen are linked with a double bond;

$R'_{11}$ is hydrogen, $C_1$-$C_6$ alkyl, isopropyl or trifluoromethyl, $R_{14}$ is phenyl, wherein the b-position carbon and the d-position nitrogen are linked with a double bond, and the d-position nitrogen and $R_{14}$ are linked with a single bond;

(B):

$R_{21}$, $R_{22}$ and $R_{23}$ are each independently hydrogen or C1-C6 alkyl;

$R_{11}$ is hydrogen, C1-C6 alkyl, isopropyl or trifluoromethyl, $R_{13}$ is phenyl, wherein $R_{11}$ and a-position carbon are linked with a single bond, and the a-position carbon and the c-position nitrogen are linked with a double bond;

$R'_{11}$ is hydrogen, C1-C6 alkyl, isopropyl or trifluoromethyl, $R_{14}$ is C(R')R'', R' is C1-C6 alkyl, isopropyl or trifluoromethyl, R'' Is phenyl, wherein the b-position carbon and the d-position nitrogen are linked with a single bond, and the d-position nitrogen and $R_{14}$ are linked with a double bond;

(C):

$R_{21}$ and $R_{11}$, and $R_{11}$ and $R_{13}$ are respectively connected to aromatic rings, which together form a fused ring structure;

$R_{23}$ and $R'_{11}$ are linked to form a cycloalkyl structure, and $R_{14}$ is phenyl, wherein the b-position carbon and the d-position nitrogen are linked with a double bond, and $R_{14}$ and d-position nitrogen are linked with a single bond.

According to embodiments of the present invention, the main catalyst has a structure of formula (IA), (IB) or (IC) as shown below.

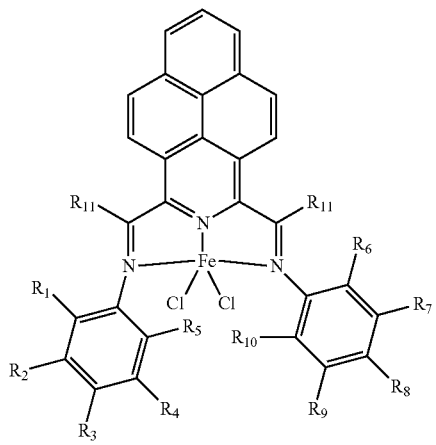

(IA)

wherein $R_1$ to $R_{10}$ are each independently selected from hydrogen, C1-C6 alkyl, halogen and C1-C6 alkoxy; $R_{11}$ is C1-C6 alkyl, isopropyl or trifluoromethyl;

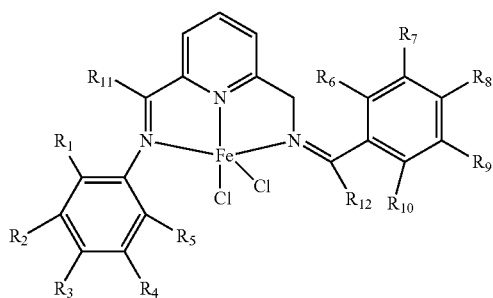

(IB)

wherein $R_1$ to $R_{10}$ are each independently selected from hydrogen, C1-C6 alkyl, halogen and C1-C6 alkoxy; $R_{11}$ is C1-C6 alkyl, isopropyl or trifluoromethyl; $R_{12}$ is C1-C6 alkyl, isopropyl or trifluoromethyl;

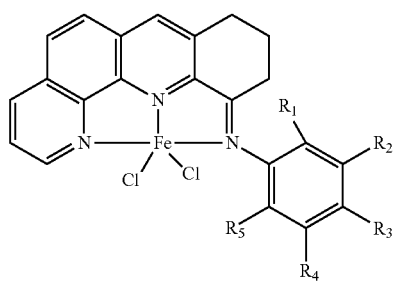

(IC)

wherein, $R_1$ to $R_5$ are each independently selected from hydrogen, C1-C6 alkyl, halogen and C1-C6 alkoxy.

The main catalyst can be divided into three types in preparation:

The first type is a derivative of pyridine and phenalene, and the catalyst is obtained by forming a ring from phenalene and substituted pyridine;

The second type is a pyridine derivative, and the catalyst is obtained from the reaction of substituted aniline and 2-acetyl-6-methylaminopyridine and, which is prepared from pyridine as raw material in several steps;

The third type is a derivative of phenanthroline, and the catalyst is obtained from the reaction of substituted aniline and 9,10-dihydrobenzo[b][1,10]phenanthroline-11(8H)-one, which is prepared from [1,10] phenanthroline in several steps.

The co-catalyst is a mixture consisting of methylaluminoxane, triisobutylaluminum and borane or $GaCl_3$. Wherein, the molar ratio of methylaluminoxane to triisobutylaluminum is from 100:1 to 1:1, in particular from 90:1 to 10:1. The molar ratio of $GaCl_3$ to methylaluminoxane and triisobutylaluminum is 1:100:10 to 1:10000:100.

The present invention provided a method of using the iron-based catalyst composition to catalyze ethylene oligomerization for manufacturing linear α-olefins, the method comprising: under anhydrous and oxygen-free conditions with ethylene pressure of 0.1~20 MPa and reaction temperature of 0-100° C., sequentially adding organic solvent (hexane or cyclohexane), a solution of the co-catalyst and a solution of the main catalyst, reaction being run for 5 to 60 minutes, and cooled to −10° C.~0° C., and methanol being added to terminate the reaction, and product being separated by distillation to give a linear α-olefin having selectivity >97% in weight and carbon distribution between C4-C28 with component of C6-C20 being greater than 80% in weight.

In the method of using the iron-based catalyst composition, the organic solvent can be petroleum ether, toluene or xylene, solvent of the solution of the main catalyst can be 1,2-dichloroethane, dichloromethane, trichloride methane, o-dichlorobenzene, hexane or cyclohexane, and the molar ratio of the co-catalyst to the main catalyst on the basis of Al/Fe is 5,000:1 to 500:1; preferably 1000:1 to 500:1.

DETAILED DESCRIPTION OF THE EMBODIMENTS

Example 1: 2,6-Dicarboxylic Acid-Pyridine and Phenalene as Substrate

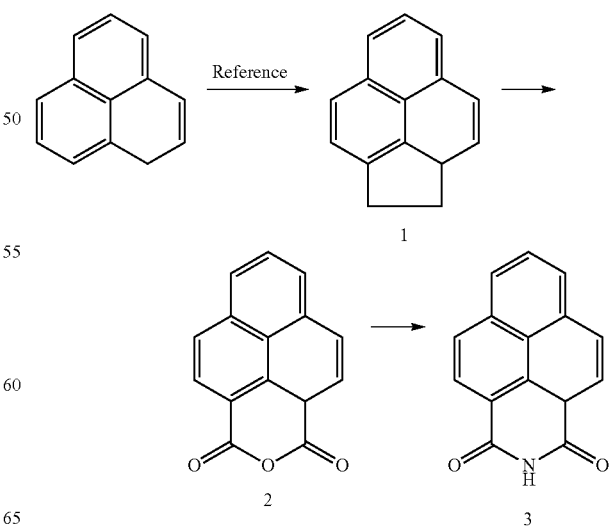

The compound 1 was prepared in reference to the method reported in *Chemische Berichte., Vol* 20, P662. Compound 1 (10 g, 0.052 mol) was dissolved in 100 mL of acetic acid. AlCl$_3$ (35 g, 0.26 mol) was added and the reaction solution was heated under reflux for 2 hours. When the starting materials were consumed as indicated by TLC, the reaction was terminated by quenching with ice water, the resulting materials were extracted with methylene chloride, organic phases were dried with anhydrous sodium sulfate and evaporated to remove the solvent, and the residue was separated by column chromatography (eluent being petroleum ether and ethyl acetate) to obtain a purified compound 2 (9 g, 73%). $^1$H NMR (CHCl$_3$ d$^3$) δppm: 8.06 (d, 1H, Aromatic H), 7.72(d,1H, Aromatic H),7.52 (d, 1H, Aromatic H),7.35 (d, 1H, Aromatic H), 7.24 (d, 1H, Aromatic H), 6.31 (d, 1H, Aromatic H), 6.23 (d, 1H, Aromatic H), 4.29 (d, 1H).

Compound 2 (9 g, 0.038 mol) was dissolved in 50 mL of methanol, cooled to 0° C., ammonia (1.6 g, 0.045 mol (was added, and the reaction was run for 2 hours, and then the reaction was stopped and the solvent was removed to give compound 3 (8.93 g, 100%). $^1$H NMR (CHCl$_3$d$^3$) δppm: 10.0 (s, 1H, NH—), 7.88 (d, 1H, Aromatic H), 7.69 (d,1H, Aromatic H), 7.52 (d, 1H, Aromatic H), 7.35 (d, 1H, Aromatic H), 7.24 (d, 1H, Aromatic H), 6.31 (d, 1H, Aromatic H), 6.23 (d, 1H, Aromatic H), 4.40 (d, 1H).

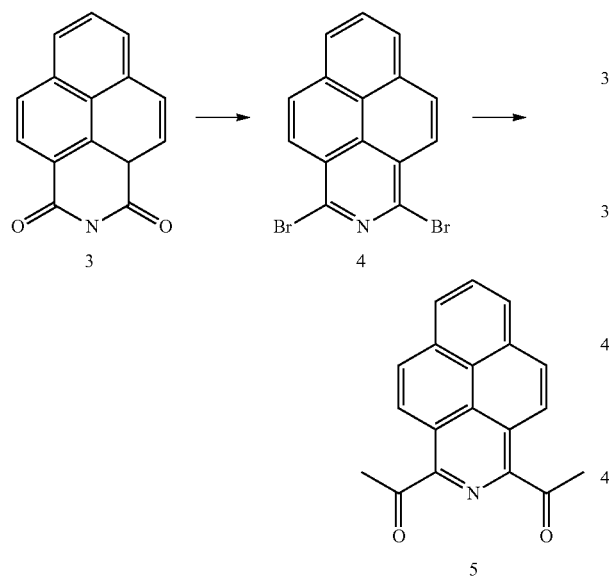

Compound 3 (8 g, 0.034 mol) was dissolved in 50 mL of toluene, phosphorus tribromide (46 g, 0.17 mol) was added and the reaction was refluxed for 2 hours. After cooling, the solvent was evaporated to dryness and purified by column chromatography to give compound 4 (11 g, 90%). $^1$H NMR (CHCl$_3$ d$^3$) δppm: 8.08 (d, 2H, Aromatic H) 7.62 (d, 2H, Aromatic H), 7.39 (d, 2H, Aromatic H), 7.32 (d, 2H, Aromatic H).

As an example, when R$_{11}$ is a methyl group: Compound 4 (10 g, 0.028 mol) was dissolved in THF (50 mL), cooled to −78° C., and butyllithium (0.06 mol) was added dropwise. After completion of the dropwise addition, the mixture was heated to room temperature and DMAC (21 g, 0.29 mol) was added. The temperature was raised to 50° C. for 2 hours, and the reaction was stopped, quenched by addition of ammonium chloride solution, and the organic phase was extracted with dichloromethane and was dried over anhydrous sodium sulfate, filtered and evaporated to dryness. Ethanol was used for recrystallization to give pure compound 5 (3.5 g, 48%). $^1$H NMR (CHCl$_3$ d$^3$) δppm 8.45 (d, 2H, Aromatic H), 7.73 (d, 2H, Aromatic H), 7.49 (d, 2H, Aromatic H), 7.32 (d, 2H, Aromatic H), 2.55 (s, 6H, CH$_3$CO—).

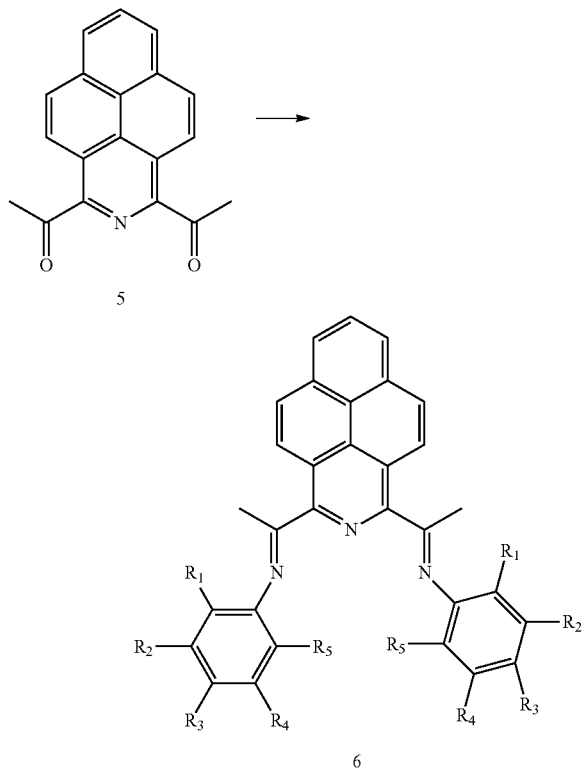

The compound 5 and the substituted aniline were reacted under anhydrous and oxygen-free conditions, wherein the molar ratio of compound 5 to substituted aniline is 1:1.2 and the solvent is toluene, the reaction was refluxed with p-toluenesulfonic acid as the catalyst. the reaction was run for 3-6 hours monitored with TLC, after the reaction was completed, the solvent was removed under reduced pressure, and the residue was separated by column chromatography (with petroleum ether and ethyl acetate as eluent) to give the target compound 6. The anilines used in the method of the present invention may be selected from: 2-methylaniline, 3-methylaniline, 4-methylaniline, 2,3-dimethylaniline, 2,4-dimethylaniline, 2,5 Aniline, 2,6-dimethylaniline, 3,4-dimethylaniline, 3,5-dimethylaniline, 3,6-dimethylaniline, 2,4,6-trimethylaniline, 4 Bromo-2,6-dimethylaniline, 2-ethylaniline, 2-ethyl-6-methylaniline, 2-fluoroaniline, 2-fluoro-4-methylaniline, 2,3,4-trifluoroaniline, 2,4,5-trifluoroaniline, 2,4,6-trifluoroaniline, and 2,3,4,5,6-pentafluoroaniline; wherein, 4-methylaniline is most preferable.

Here 4-methyl aniline is taken as an example: Compound 5 (1 g, 3.85 mmol) was dissolved in 50 ml of toluene and 1.2 eq of 4-methylaniline was added dropwise. After addition of 0.1 eq of p-toluenesulfonic acid, the reaction was refluxed, and, after 3 hours the reaction was completed as indicated by TLC. The reaction was stopped and the solvent was removed under reduced pressure. The residue was purified by column chromatography to give compound 6 (1.35 g, 80%) with R3 being methyl. $^1$H NMR (CHCl$_3$ d$^3$) δppm: 7.87 (d, 2H, Aromatic H) 7.50 (d, 2H, Aromatic H),7.49 (d, 2H, Aromatic H), 7.32 (d, 1H, Aromatic H), 7.1 (m, 8H, Aromatic H), 2.35 (s, 6H, C$\underline{H}_3$), 0.9 (s, 6H, C$\underline{H}_3$N—).

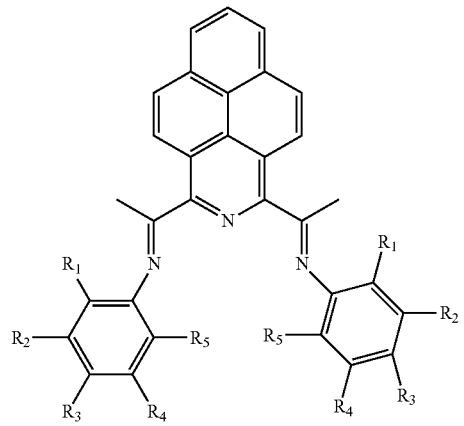

6

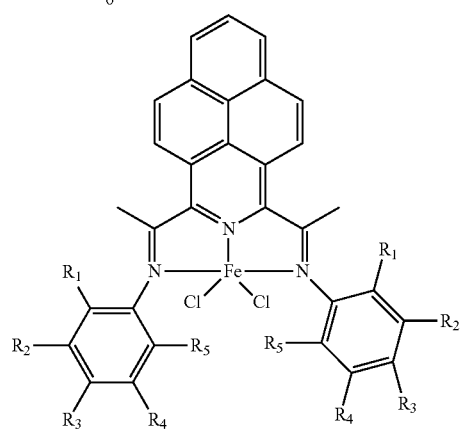

7

Here, 4-methyl aniline, 4-methyl benzaldehyde is taken as an example: Compound 6 (1 g, 2.3 mmol) was dissolved in 50 ml of toluene under inert gas protection, the oxygen in the solvent being removed with the inert gas, and ferrous chloride (5.2 g, 4.08 mmol) was added. The reaction was stirred overnight under the inert gas protection, and the reaction was completed as indicated by TLC. The resulting materials were filtrated, solvent was evaporated, and the residue was washed with ether to give compound 7 (0.89 g, 68%). $^1$H NMR (CHCl$_3$ d$^3$) δppm: 7.90 (d, 2H, Aromatic H), 7.50 (d, 2H, Aromatic H), 7.49 (d, 2H, Aromatic H), 7.32 (d, 1H, Aromatic H), 7.1 (m, 8H, Aromatic H), 2.35 (s, 6H, C$\underline{H}_3$), 0.9 (s, 6H, C$\underline{H}_3$N—).

Example 2: 2-Acetyl-6-Methylamino as Substrate

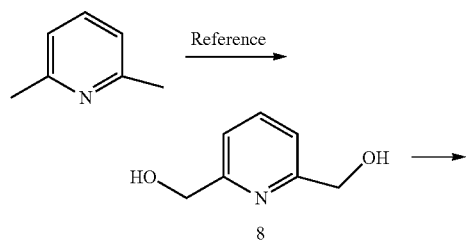

8

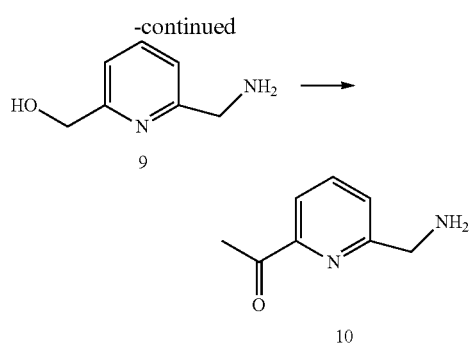

Compound 8 was prepared in reference to the method reported in *Synthetic Communications,* 2005, 35,2317-2324, and was prepared by using 2,6-lutidine as a starting material followed by oxidation and reduction. Compound 8 (10 g, 0.07 mol) was dissolved in dichloromethane, cooled to 0° C. and then ammonia (1.2 g, 0.079 mol) was added. After stirring for half an hour, the reaction was stopped and the solvent was evaporated. The residue was separated by column chromatography to give mono-substituted compound 9 (5.8 g, 60%). $^1$NMR (CHCl$_3$ d$^3$) δppm:8.12(m,1H, Aromatic H), 7.66 (m, 1H, Aromatic H), 7.60 (m, 1H, Aromatic H), 5.12 (m, 2H, C$\underline{H}_2$—), 4.24 (m, 2H, C$\underline{H}_2$—).

Compound 9 (5 g, 0.036 mol) was dissolved in dichloromethane, PCC oxidant (8.6 g, 0.04 mol) was added, and the reaction was run at room temperature for 2 hours. When the reaction was completed as indicated by TLC, the reaction was stopped and the solvent was evaporated. After column chromatography, a compound having an aldehyde group at the 2-position was obtained, which compound was then dissolved in dichloromethane, cooled to −78° C., and a dimethyl lithium solution (1.1 eq) was added dropwise. The reaction was further run for 2 hours, and an ammonium chloride solution was added to quench the reaction. The organic phase was extracted with methylene chloride, dried, evaporated to dryness, and separated by column chromatography to give compound 10 (4.5 g, 92%). $^1$H NMR (CHCl$_3$ d$^3$) δppm: 8.24(m,1H, Aromatic H), 8.22 (m, 1H, Aromatic H), 8.08 (m, 1H, Aromatic H), 4.24 (m, 2H, C$\underline{H}_2$—), 2.36 (s, 3H, C$\underline{H}_3$CO—).

Compound 10 was reacted with substituted aniline under anhydrous and oxygen-free conditions, wherein the molar ratio of compound 10 to substituted aniline is 1:1.2 and the solvent is toluene, the reaction was refluxed with p-toluenesulfonic acid as the catalyst. The reaction was run for 3-6 hours and monitored by TLC. After the reaction is completed, the solvent was removed under reduced pressure, and then residue was separated by column chromatography (with petroleum ether and ethyl acetate as eluent) to give the target compound 11.

The substituted aniline used herein may be selected from: 2-methylaniline, 3-methylaniline, 4-methylaniline, 2,3-dimethylaniline, 2,4-dimethylaniline, 2,5 Aniline, 2,6-dimethylaniline, 3,4-dimethylaniline, 3,5-dimethylaniline, 3,6-dimethylaniline, 2,4,6-trimethylaniline, 4 Bromo-2,6-dimethylaniline, 2-ethylaniline, 2-ethyl-6-methylaniline, 2-fluoroaniline, 2-fluoro-4-methylaniline, 2,3,4-trifluoroaniline, 2,4,5-trifluoroaniline, 2,4,6-trifluoroaniline and 2,3,4,5,6-pentafluoroaniline; wherein, 4-methylaniline is most preferable.

Here, taking 4-methyl aniline as an example: Compound 10 (1 g, 7 mmol) was dissolved in 50 ml of toluene and 1.2 eq of 4-methylaniline was added dropwise. Then 0.1 eq of p-toluenesulfonic acid was added, and the reaction was refluxed for 3 hours, the reaction was completed as indicated by TLC. The reaction was stopped and the solvent was removed under reduced pressure. The residue was purified by column chromatography to give compound 11 (1.3 g, 85%) with $R_3$ being methyl. $^1$H NMR (CHCl$_3$ d$^3$) δppm: 8.06 (m,1H, Aromatic H), 7.93 (m, 1H, Aromatic H), 7.82 (m, 1H, Aromatic H), 4.24 (m, 2H, C$\underline{H}_2$—), 2.35 (s, 3H, C$\underline{H}_3$—), 0.9 (s, 3H, C$\underline{H}_3$N—).

Compound 11 was reacted with substituted benzophenone under anhydrous and oxygen-free conditions, wherein the molar ratio of the compound 11 to the substituted aniline is 1:1.2 and the solvent is toluene and, the reaction was refluxed with p-toluenesulfonic acid as the catalyst. The reaction was run for 3-6 hours and monitored by TLC. After the reaction is completed, the solvent was removed under reduced pressure, and then the residue is separated by column chromatography (petroleum ether and ethyl acetate as eluent) to give the target compound 12.

The substituted benzophenone used herein may be selected from 2-methylacetophenone, 3-methylacetophenone, 4-methylacetophenone, 2,3-dimethylacetophenone, 2,4-dimethyl acetophenone, 2,5-dimethylacetophenone, 2,6-dimethylacetophenone, 3,4-dimethylacetophenone, 3,5-dimethylacetophenone, 3,6-dimethylacetophenone, 2,4,6-trimethylacetophenone, 4-bromo-2,6-dimethylacetophenone, 2-ethylacetophenone, 2-fluoroacetophenone, 2-fluoro-4-methylacetophenone, 2,3,4-trifluoroacetophenone, 2,4,5-trifluorophenethyl ketone, 2,4,6-trifluoroacetophenone, 2,3,4,5,6-pentafluoroacetophenone, 2-methylphenylacetone, 3-methylphenylacetone, 4-methylphenylacetone, 2,3-dimethylphenylacetone, 2,4-dimethylphenylacetone, 2,5-dimethylphenylacetone, 2,6-dimethylphenylacetone, 3,4-dimethylphenylacetone, 5-dimethylphenylacetone, 3,6-dimethylphenylacetone, 2,4,6-trimethylphenylacetone, 4-bromo-2,6-dimethylphenylacetone, 2-ethylphenylacetone 2-ethyl-6-methylphenylacetone, 2-fluorophenylacetone, 2-fluoro-4-methylphenylacetone, 2,3,4-trifluorophenylacetone, 2,4,5-trifluorophenylacetone, 2,4,6-trifluorophenylacetone, 2,3,4,5,6-pentafluorophenylacetone, 2-methyl trifluoroacetophenone, 3-methyl trifluoroacetophenone, 4-methyl trifluoroacetophenone, 2,3-dimethyl trifluoroacetophenone, 2,4-dimethyl trifluoroacetophenone, 2,5-dimethyl trifluoroacetophenone, 2,6-dimethyl trifluoroacetophenone, 3,4-dimethyl trifluoroacetophenone, 3,5-dimethyl trifluoroacetophenone, 3,6-dimethyl trifluoroacetophenone, 2,4,6-trimethyl trifluoroacetophenone, 4-bromo-2,6-dimethyltrifluoroacetophenone, 2-ethyl Trifluoroacetophenone, 2-ethyl-6-methyl trifluoroacetophenone, 2-fluoro trifluoroacetophenone, 2-fluoro-4-methyl trifluoroacetophenone, 2,3,4-tris Trifluoroacetophenone, 2,4,6-trifluoro trifluoroacetophenone, and 2,3,4,5,6-pentafluorotrifluorobenzene ethanone; wherein, 4-methylacetophenone is most preferable.

Here, taking 4-methyl acetophenone as an example: Compound 11 (1 g, 4 mmol) was dissolved in 50 ml of toluene and 1.2 eq equivalent of 4-methylacetophenone was added dropwise. Then 0.1 eq of p-toluenesulfonic acid was added dropwise, and the reaction was refluxed, and after 3 hours the reaction was completed as indicated by TLC. The reaction was stopped and the solvent was removed under reduced pressure. Purification by column chromatography gave compound 12 (1.2 g, 90%) with $R_8$ as methyl. $^1$H NMR (CHCl$_3$ d$^3$) δppm: 8.11 (s, 1H, C$\underline{H}$N—), 7.98(m,1H, Aromatic H), 7.86 (m, 1H, Aromatic H), 7.51 (m, 3H, 芳环 H), 7.09 (m, 2H, Aromatic H), 5.14 (m, 2H, C$\underline{H}_2$—), 2.35 (s, 6H, C$\underline{H}_3$—), 0.9 (s, 3H, C$\underline{H}_3$N—).

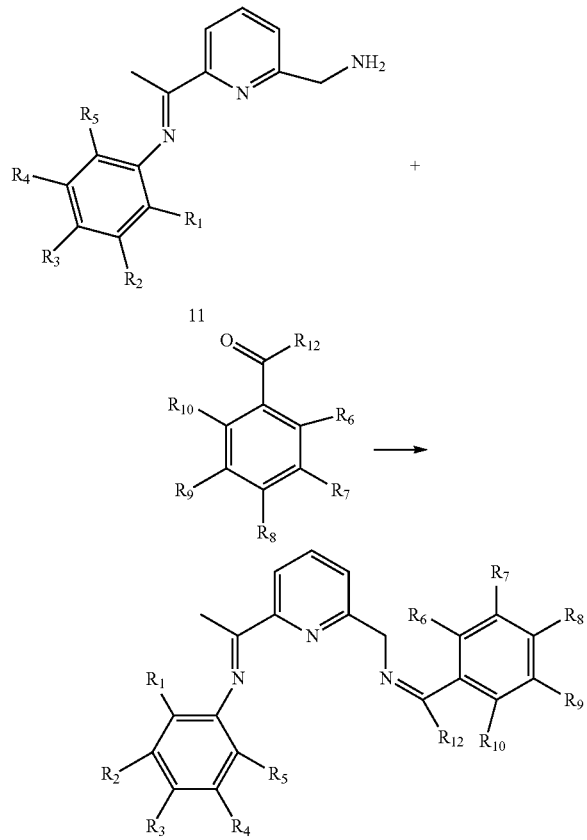

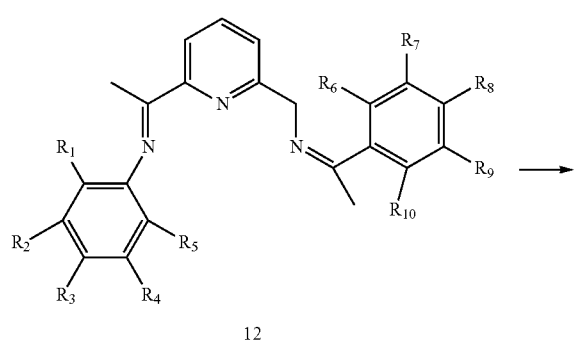

12

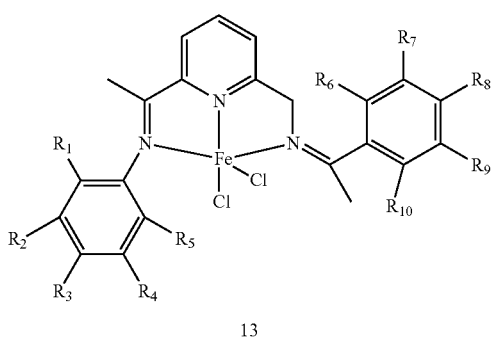

13

Here, taking 4-methyl aniline and 4-methyl acetophenone as an example. Compound 12 (1 g, 3 mmol) was dissolved in 50 ml of toluene under protection of an inert gas, with oxygen in the solvent being removed with the inert gas, and ferrous chloride (4.5 g, 3.55 mmol) was added. The reaction was stirred overnight under the inert gas protection, and the reaction was completed as indicated by TLC. The resulting materials were filtrated, solvent was evaporated, and the residue was washed with ether to give compound 13 (13 g, 88%). $^1$H NMR (CHCl$_3$ d$^3$) δppm: 7.98 (m,1H, Aromatic H), 7.86 (m, 1H, Aromatic H)), 7.51 (m, 3H, Aromatic H), 7.50 (s, 1H, C$\underline{H}$N—), 7.10 (m, 2H, Aromatic H), 5.10 (m, 2H, C$\underline{H}_2$—), 2.35 (s, 6H, C$\underline{H}_3$—), 0.9 (s, 3H, C$\underline{H}_3$N—).

Example 3: Phenanthroline as Substrate

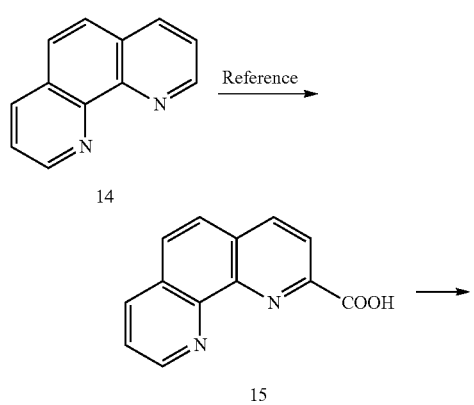

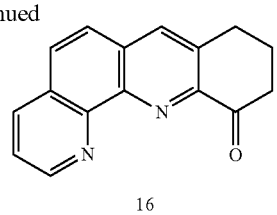

16

The compound 15 was prepared with reference of the method reported in Organometallics, 25 (3), 2006, and was prepared two steps from 1,10-phenanthroline as a starting material.

Compound 15 (2.2 g, 1 mmol) was dissolved in dichloromethane and then 1.1 eq of thionyl chloride was added dropwise. Then the mixture was stirred for 2 hours. AlCl$_3$ (2 g, 1.5 mmol) and 3-chlorobromide propane (1.57 g, 1.1 mmol) were added, and the reaction was run at room temperature for 1 hour and then heated to reflux overnight. After cooling, the reaction was poured into ice water and extracted with dichloromethane. The organic phase was dried over anhydrous sodium sulfate, filtered and evaporated to give crude product, which was recrystallized from petroleum ether and ethyl acetate to give compound 16 as a white solid (1.4 g, 56%). $^1$H NMR (CHCl$_3$ d$^3$) δppm:8.81 (m,1H, Aromatic H), 8.00 (m,1H, Aromatic H), 7.87(s, 1H, Aromatic H), 7.68(m, 1H, Aromatic H), 7.43(m, 1H, Aromatic H), 7.26 (m, 1H, Aromatic H), 2.55 (m, 2H, C$\underline{H}_2$—), 2.40 (m, 2H, C$\underline{H}_2$—), 1.95 (m, 2H, C$\underline{H}_2$—).

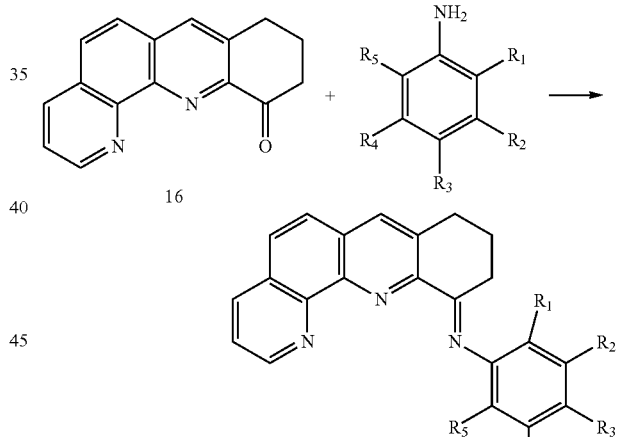

The compound 16 was reacted with substituted aniline under anhydrous and oxygen-free conditions, wherein the molar ratio of compound 16 to substituted aniline is 1:1.2, and the solvent is toluene, the reaction was refluxed with p-toluenesulfonic acid as a catalyst. The reaction was run for 3-6 hours and monitored by TLC. After the reaction is completed, the solvent was removed under reduced pressure, and then the residue was separated by column chromatography (petroleum ether and ethyl acetate as eluent) to give the compound 17.

The substituted aniline used herein may be selected from:2-methylaniline, 3-methylaniline, 4-methylaniline, 2,3-dimethylaniline, 2,4-dimethylaniline, 2,5 Aniline, 2,6-dimethylaniline, 3,4-dimethylaniline, 3,5-dimethylaniline, 3,6-dimethylaniline, 2,4,6-trimethylaniline, 4 Bromo-2,6-dimethylaniline, 2-ethylaniline, 2-ethyl-6-methylaniline, 2-fluoroaniline, 2-fluoro-4-methylaniline, 2,3,4-trifluoroaniline, 2,4,5-trifluoroaniline, 2,4,6-trifluoroaniline, 2,3,4,5,6-pentafluoroaniline; wherein,4-methylaniline is most preferable.

Here, taking 4-methyl aniline as an example: Compound 16 (1 g, 4 mmol) was dissolved in 50 ml of toluene and 1.2 eq of 4-methylaniline was added dropwise. Then 0.1 eq of p-toluenesulfonic acid was added, and the reaction was refluxed for 3 hours, the reaction was completed as indicated by TLC. The reaction was stopped and the solvent was removed under reduced pressure. The residue was purified by column chromatography to give compound 17 (1.1 g, 80%) with $R_3$ being methyl. $^1$H NMR (CHCl$_3$ d$^3$) δppm:8.81 (m,1H, Aromatic H), 8.03 (m,1H, Aromatic H), 8.00 (m,1H, Aromatic H), 7.68 (m, 1H, Aromatic H), 7.43 (m, 1H, Aromatic H), 7.26 (m, 1H, Aromatic H),7.1 (m, 4H, Aromatic H), 2.55 (m, 2H, C$\underline{H}_2$—), 2.35 (s, 3H, C$\underline{H}_3$—), 1.70 (m, 2H, C$\underline{H}_2$—), 1.30 (m, 2H, C$\underline{H}_2$—).

Here, taking 4-methyl aniline as an example: Compound 17 (1 g, 3 mmol) was dissolved in 50 ml of toluene under the protection of an inert gas, with oxygen in the solvent being removed with the inert gas, and ferrous chloride (4.5 g, 3.55 mmol) was added. The reaction was stirred overnight under the inert gas protection, and the reaction was completed as indicated by TLC. The resulting materials were filtered, solvent was evaporated, and the the residue was washed with ether to give compound 18 (1.1 g, 80%). $^1$H NMR (CHCl$_3$ d$^3$) δppm:8.81(m,1H, Aromatic H), 8.00 (m,2H, Aromatic H), 7.70 (m, 1H, Aromatic H), 7.40 (m, 1H, Aromatic H), 7.30 (m, 1H, Aromatic H), 7.1 (m, 4H, Aromatic H), 2.55 (m, 2H, C$\underline{H}_2$—), 2.35 (s, 3H, C$\underline{H}_3$—), 1.70 (m, 2H, C$\underline{H}_2$—), 1.30 (m, 2H, C$\underline{H}_2$—).

Experiments and Methods of Ethylene Oligomerization Reaction

A dried 250 mL three-necked flask equipped with a magnetic stirrer was vacuumed with heating, and, after replacement with nitrogen for several times, was filled with ethylene, followed by addition of toluene, the co-catalyst MAO and the catalyst. The reaction was run at a predetermined temperature. The pressure was kept constant by automatic adjustment through a solenoid valve, and the change in pressure with time in the buffer tank was recorded. The polymerization was carried out for 30 min, and the reaction was terminated by using methanol or acidified ethanol with mass fraction of 10%. The product of ethylene oligomerization was analyzed by GC-MS, and the activity of the catalyst was determined by the pressure drop of the ethylene buffer tank.

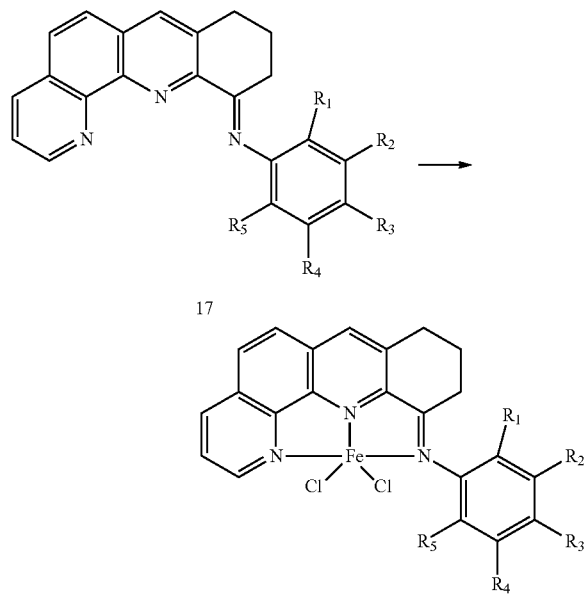

17

18

Examples of the Results of Ethylene Oligomerization

Some of the experimental results are listed in the table below.

| Sample. | Catalyst | Al/Fe molar ratio | Rxn temp., °C. | Rxn press., MPa | Rxn time, min | Catalytic activity, Kg/mol·h | Selectivity, $C_6$—$C_{20}$, wt % | $C_4$, wt % | $C_6$, wt % | $C_8$, wt % | $C_{10}$, wt % | $C_{12}$, wt % | $C_{14}$—$C_2$ wt % | $C_{20+}$ wt % |
|---|---|---|---|---|---|---|---|---|---|---|---|---|---|---|
| 1 | 7-1 | 2000 | 50 | 0.1 | 30 | 10800 | 75.8 | 10 | 14 | 16 | 12.5 | 10 | 23.3 | 14.2 |
| 2 | 7-2 | 2000 | 50 | 0.1 | 30 | 9800 | 78.0 | 12 | 18 | 16 | 14 | 12 | 18 | 10 |
| 3 | 7-3 | 2000 | 50 | 0.1 | 30 | 12300 | 80.0 | 14 | 20 | 18 | 16 | 12 | 14 | 6 |
| 4 | 13-1 | 2000 | 50 | 0.1 | 30 | 87800 | 76.5 | 12 | 14.5 | 17 | 13 | 11.2 | 20.8 | 11.5 |
| 5 | 13-2 | 2000 | 50 | 0.1 | 30 | 10200 | 79.8 | 13 | 20 | 18 | 16 | 14 | 11.8 | 7.2 |
| 6 | 13-3 | 2000 | 50 | 0.1 | 30 | 11000 | 82.1 | 14 | 23 | 20 | 18 | 16 | 5.1 | 3.9 |
| 7 | 18-1 | 2000 | 50 | 0.1 | 30 | 9780 | 78.8 | 13 | 18 | 17 | 15.6 | 12.8 | 15.4 | 8.2 |
| 8 | 18-2 | 2000 | 50 | 0.1 | 30 | 12000 | 80.9 | 14 | 17 | 17 | 16 | 14 | 16.9 | 5.1 |
| 9 | 18-3 | 2000 | 50 | 0.1 | 30 | 11100 | 83.5 | 14 | 24 | 22 | 16 | 14 | 7.5 | 2.5 |
| 10 | 19 | 2000 | 50 | 0.1 | 30 | 10500 | 76.0 | 12 | 14 | 16 | 14 | 12 | 20 | 12 |

-continued

| Sample | Catalyst | Al/Fe molar ratio | Rxn temp., °C | Rxn press., MPa | Rxn time, min | Catalytic activity, Kg/mol·h | Selectivity, $C_6$—$C_{20}$, wt % | $C_4$, wt % | $C_6$, wt % | $C_8$, wt % | $C_{10}$, wt % | $C_{12}$, wt % | $C_{14}$—$C_2$ wt % | $C_{20+}$, wt % |
|---|---|---|---|---|---|---|---|---|---|---|---|---|---|---|
| 11 | 20 | 2000 | 50 | 0.1 | 30 | 10000 | 68.5 | 8 | 10 | 12 | 12 | 10 | 24.5 | 23.5 |
| 12 | 21 | 2000 | 50 | 0.1 | 30 | 9650 | 66.5 | 6 | 8 | 10 | 12 | 10 | 26.5 | 27.5 |

Notes:

1. The reaction conditions of ethylene oligomerization: The catalyst is in a concentration of 5 μmol, the solvent is 50 mL toluene, the co-catalyst is MAO;

2. The content of alpha olefin is greater than 99% and the selectivity of linear alpha olefin is greater than 96%.

3. The structure of each catalyst are described below:

A. The catalysts 7-1 to 7-3 are: The main catalyst (Compound 7 provided in Example 1 of this specification) as shown in the following structural formula, where, $R_{11}$ is methyl, $R_1$, $R_2$ and $R_4$ and $R_6$, $R_7$, $R_9$ are hydrogen. Catalyst 7-1: $R_3$ and $R_8$ are methoxy, $R_5$ and $R_{10}$ are methyl. Catalyst 7-2: $R_3$ and $R_8$ are methyl, $R_5$ and $R_{10}$ are hydrogen. Catalyst 7-3: $R_5$ and $R_{10}$ are bromine, $R_3$ and $R_8$ are hydrogen.

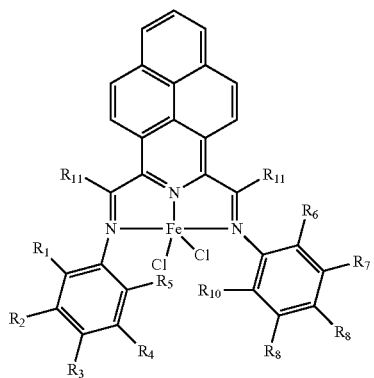

B. Catalysts 13-1 to 13-3 are: The main catalyst (Compound 13 provided in Example 2 of this specification) as shown in the following structural formula, wherein, $R_{11}$ and $R_{12}$ are methyl, $R_2$, $R_4$, $R_5$ and $R_7$, $R_9$, $R_{10}$ is hydrogen. Catalyst 13-1: $R_1$ and $R_6$ are methoxy, and $R_3$ and $R_8$ are methyl. Catalyst 13-2: $R_3$ and $R_8$ are methyl, and $R_1$ and $R_6$ are hydrogen. Catalyst 13-3: $R_1$ and $R_6$ are bromine, $R_3$ and $R_8$ are hydrogen.

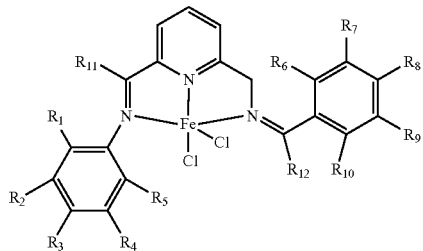

C. Catalysts 18-1 to 18-3 are: Main catalyst (Compound 18 provided in Example 3 of the this specification) as shown in the following structural formula, wherein, $R_2$ and $R_4$ are hydrogen. Catalyst 18-1: $R_3$ is methoxy, and $R_1$ and $R_5$ are methyl. Catalysts 18-2: $R_3$ and $R_5$ are methyl, and $R_1$ is hydrogen. Catalyst 18-3: $R_1$ is bromine, $R_5$ is methyl, and $R_3$ is hydrogen.

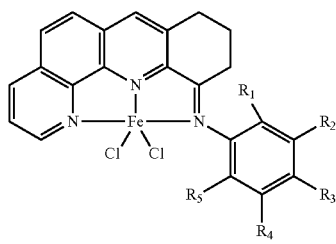

-continued

| Sample. | Catalyst | Al/Fe molar ratio | Rxn temp., °C. | Rxn press., MPa | Rxn time, min | Catalytic activity, Kg/mol·h | Selectivity, $C_6$—$C_{20}$, wt % | $C_4$, wt % | $C_6$, wt % | $C_8$, wt % | $C_{10}$, wt % | $C_{12}$, wt % | $C_{14}$—$C_2$ wt % | $C_{20+}$, wt % |
|---|---|---|---|---|---|---|---|---|---|---|---|---|---|---|

D. Catalysts 19 to 21 are control examples: The three catalysts described in J. Am. Chem. Soc. 1998, 120, 7143-7144, and the main catalyst is shown in the following structural formula, wherein, the catalyst 19 is of the formula 7 with R being methyl; the catalyst 20 is of the formula 8 with R being ethyl; the catalyst 21 is of the formula 9 with R being isopropyl.

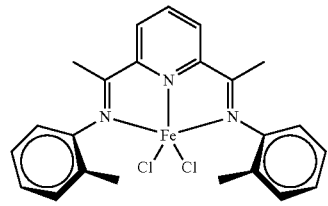

7

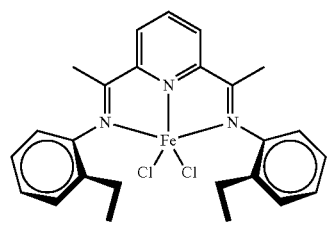

8

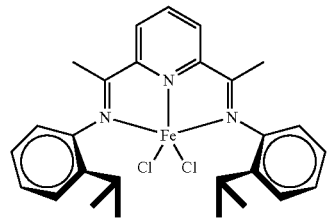

9

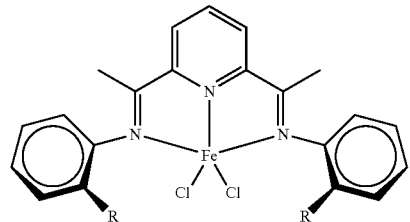

1 R = Me
2 R = Et
3 R = i-Pr

In the above embodiments and examples, the objects, technical features and advantages of the invention has been described in detail. It should be understood that the specific embodiments are not intended in any way to limit the invention, Any modifications, equivalent substitutions, improvements, and the like within the spirit and principles of the present invention are intended to be included within the scope of the present invention.

The invention claimed is:

1. A linear poly-α-olefin catalyst, comprising a main catalyst and a co-catalyst,
wherein the main catalyst has a structure of formula (IA), (IB) or (IC) below:

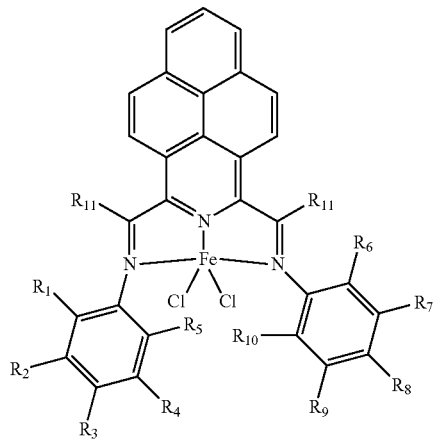

(IA)

wherein $R_1$ to $R_{10}$ are each independently selected from hydrogen, C1-C6 alkyl, halogen and C1-C6 alkoxy; $R_{11}$ is C1-C6 alkyl, isopropyl or trifluoromethyl;

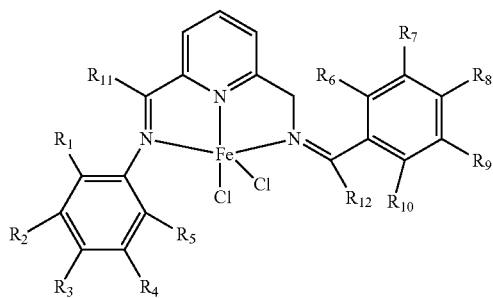

(IB)

wherein $R_1$ to $R_{10}$ are each independently selected from hydrogen, C1-C6 alkyl, halogen and C1-C6 alkoxy; $R_{11}$ is C1-C6 alkyl, isopropyl or trifluoromethyl; $R_{12}$ is C1-C6 alkyl, isopropyl or trifluoromethyl;

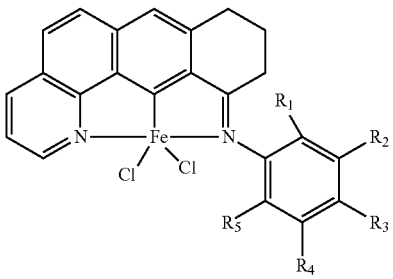

(IC)

wherein, $R_1$ to $R_5$ are each independently selected from hydrogen, C1-C6 alkyl, halogen and C1-C6 alkoxy.

2. The catalyst of claim 1, wherein the main catalyst has formula (IA), and is obtained by reacting 2,6-diacetyl-pyridine phenalene with substituted aniline.

3. The catalyst of claim 1, wherein the main catalyst has formula (IB), and is obtained by reacting 2-acetyl-6-methylamino with substituted aniline.

4. The catalyst of claim 1, wherein the main catalyst has formula (IC), and is obtained by reacting 9,10-dihydrobenzo[b][1,10]phenanthroline-11(8H)-one with substituted aniline, wherein the 9,10-dihydrobenzo[b][1,10]phenanthroline-11 (8H)-one is prepared from [1,10] phenanthroline.

5. The catalyst of claim 1, wherein any one of the terminal phenyl end-groups is mono-, di- or tri-substituted by C1-C4 alkyl, and is selected from the group consisting of 2-methylphenyl, 4-methylphenyl, 2,4-dimethylphenyl, 2,6-dimethylphenyl, 2,4,6-trimethylphenyl, 2-ethylphenyl, 4-ethylphenyl, 2,4-diethylphenyl, 2,6-diethylphenyl, 2,4,6-triethylphenyl, 2-propylphenyl, 4-propylphenyl, 2,4-dipropylphenyl, 2,6-dipropylphenyl, 2,4,6-tripropylphenyl, 2-isopropylphenyl, 4-isopropylphenyl, 2,4-diisopropylphenyl, 2,6-diisopropylphenyl, 2,4,6-triisopropylphenyl, 2-butylphenyl, 4-butylphenyl, 2,4-dibutylphenyl, 2,6-dibutylphenyl, 2,4,6-tributylphenyl, 2-tert-butylphenyl, 4-tert-butylphenyl, 2,4-di-tert-butylphenyl, 2,6-di-, 6-tri-tert-butylphenyl, 2-tert-butylphenyl, 4-tert-butylphenyl, 2,4-di-tert-butylphenyl, 2,6-di-tert-butylphenyl, and 2,4,6-tri-tert-butylphenyl.

6. The catalyst of claim 1, wherein any one of the terminal phenyl end-groups is mono-, di- or tri-substituted with by halogen, and is selected from the group consisting of 2-chlorophenyl, 4-chlorophenyl, 2,4-dichlorophenyl, 2,4,6-trichlorophenyl, 2-bromophenyl, 4-bromophenyl, 2,4-dibromophenyl, 2,4,6-tribromophenyl, 2-fluorophenyl, 4-fluorophenyl, 2,4-difluorophenyl, and 2,4,6-trifluorophenyl.

7. The catalyst of claim 1, wherein any one of the terminal phenyl end-groups is mono-, di- or tri-substituted by halogen and/or C1-C4 alkyl, and is selected from the group consisting of 2-bromo-4-methylphenyl, 2-bromo-6-methyl phenyl, 2,6-dibromo-4-methylphenyl, 4-bromo-2,6-dimethylphenyl, 2-chloro-4-methylphenyl, 2-chloro-6-methylphenyl, 2,6-dichloro-4-methylphenyl, and 4-chloro-2,6-dimethylphenyl.

8. The catalyst of claim 1, wherein the co-catalyst is a mixture comprising methylaluminoxane, triisobutylaluminum, and borane or $GaCl_3$.

9. A method for ethylene oligomerization to linear α-olefins, the method comprising:
adding sequentially an organic solvent, a solution of the co-catalyst of claim 8 and a solution of the main catalyst of claim 8;

contacting the co-catalyst and the main catalyst with ethylene under anhydrous and oxygen-free conditions under ethylene pressure of 0.1-20 MPa and a reaction temperature of 0-100° C. for a duration of 5-60 minutes to produce an oligomerization effluent having linear α-olefin selectivity of >97 and a $C_6$-$C_{20}$ oligomers distribution being greater than 80% in weight among $C_4$-$C_{28}$ oligomers;

cooling the oligomerization effluent to −10° C.-0° C. to produce a cooled effluent, adding methanol to the cooled effluent to terminate the reaction to produce a terminated reaction product, and distilling the terminated reaction product to separate the linear α-olefin.

10. The method of claim 9, wherein the organic solvent is petroleum ether, toluene or xylene, solvent of the solution of the main catalyst is 1,2-dichloroethane, dichloromethane, trichloride methane, o-dichlorobenzene, hexane or cyclohexane, and molar ratio of the co-catalyst to the main catalyst on the basis of Al/Fe is 5,000:1 to 500:1.

* * * * *